(12) United States Patent
Lee et al.

(10) Patent No.: US 10,703,690 B2
(45) Date of Patent: Jul. 7, 2020

(54) METHOD OF PREPARING BUTADIENE (71) Applicant: LG CHEM, LTD., Seoul (KR)

(72) Inventors: Jae Ik Lee, Daejeon (KR); Eun Kyo Kim, Daejeon (KR); Mi Kyung Kim, Daejeon (KR); Jeong Seok Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/073,279

(22) PCT Filed: Dec. 18, 2017

(86) PCT No.: PCT/KR2017/014964
§ 371 (c)(1),
(2) Date: Jul. 26, 2018

(87) PCT Pub. No.: WO2018/124579
PCT Pub. Date: Jul. 5, 2018

(65) Prior Publication Data
US 2019/0330126 A1    Oct. 31, 2019

(30) Foreign Application Priority Data

Dec. 29, 2016  (KR) .................. 10-2016-0182326

(51) Int. Cl.
*C07C 5/48* (2006.01)
*B01D 5/00* (2006.01)
(Continued)

(52) U.S. Cl.
CPC .............. *C07C 5/48* (2013.01); *B01D 5/0069* (2013.01); *C07C 7/005* (2013.01); *C07C 7/04* (2013.01); *C07C 7/09* (2013.01); *C07C 7/11* (2013.01)

(58) Field of Classification Search
CPC ........... C07C 5/3332; C07C 7/04; C07C 7/00; C07C 7/20; C07C 7/12; C07C 7/09; C07C 11/16; C07C 2523/745
(Continued)

(56) References Cited

U.S. PATENT DOCUMENTS 8,933,284 B2    1/2015   Arnold et al.
2007/0244349 A1  10/2007  Crone et al.
(Continued)

FOREIGN PATENT DOCUMENTS

JP    2015061859    4/2015
JP    2016503073    2/2016
(Continued)

OTHER PUBLICATIONS

Supplementary Search Report of European Patent Office in Appl'n No. EP17886251, dated Feb. 27, 2019.
(Continued)

*Primary Examiner* — Thuan D Dang
(74) *Attorney, Agent, or Firm* — Dentons US LLP (57) ABSTRACT

The present invention relates to a method of preparing butadiene and a device for preparing the same. According to the present invention, when butadiene is prepared by oxidative dehydrogenation of butene, unlike conventional methods, in which nitrogen is used as a diluent gas and an absorption method is used to separate butadiene from reaction products, butane is used as a diluent gas and a condensation method, in which butadiene is liquefied and separated from reaction products using a low-temperature refrigerant or cooling water, is used. In addition, an absorption method of recovering all hydrocarbons from an upper stream generated in a condensation process is used, so that loss of hydrocarbons is minimized. Therefore, the method and device of the present invention may provide high-purity (Continued)

butadiene while reducing raw material costs, production costs, and energy consumption, thereby improving economic efficiency of processes.

16 Claims, 3 Drawing Sheets

(51) Int. Cl.
    *C07C 7/00*     (2006.01)
    *C07C 7/04*     (2006.01)
    *C07C 7/09*     (2006.01)
    *C07C 7/11*     (2006.01)

(58) Field of Classification Search
    USPC .................................... 585/616, 621, 624
    See application file for complete search history.

(56) References Cited

U.S. PATENT DOCUMENTS

| | | |
|---|---|---|
| 2014/0200381 A1 | 7/2014 | Josch et al. |
| 2015/0166439 A1 | 6/2015 | Bozzano et al. |

FOREIGN PATENT DOCUMENTS

| | | |
|---|---|---|
| KR | 10-2012-0103759 | 9/2012 |
| KR | 10-1256247 | 4/2013 |
| KR | 10-1655557 | 9/2016 |
| WO | 2015051028 | 4/2015 |

OTHER PUBLICATIONS

Notification of Allowance of Japanese Patent Office in Appl'n No. 2018-562641, dated Dec. 24, 2019.

METHOD OF PREPARING BUTADIENE

CROSS-REFERENCE TO RELATED APPLICATION

This application is a National Stage Application of International Application No. PCT/KR2017/014964 filed on Dec. 18, 2017, which claims priority to and the benefit of Korean Patent Application No. 10-2016-0182326, filed on Dec. 29, 2016 in the Korean Intellectual Property Office, the disclosure of which is incorporated herein in its entirety by reference for all purposes as if fully set forth herein.

TECHNICAL FIELD

The present invention relates to a method of preparing butadiene. More specifically, the present invention relates to a method of preparing high-purity butadiene, which is capable of improving economic efficiency of processes by increasing productivity while reducing energy consumption and raw material costs.

BACKGROUND ART

Butadiene, an important chemical, is used as an intermediary for various petrochemical products, and demand and value thereof are gradually increasing in the petrochemical market.

Butadiene can be extracted from the C4 fraction through naphtha cracking or obtained by direct dehydrogenation or oxidative dehydrogenation of butene.

Thereamong, according to the method of preparing butadiene by oxidative dehydrogenation of butene, oxygen is used as a reactant, and two hydrogens are removed from butene to generate butadiene. In this case, water generated as a result of the reaction is stable. Thus, the method is thermodynamically very advantageous. In addition, since oxidative dehydrogenation is an exothermic reaction unlike direct dehydrogenation, butadiene may be obtained in a high yield even at low reaction temperatures as compared with direct dehydrogenation. Therefore, using the method of preparing butadiene by oxidative dehydrogenation of butene, it is possible to effectively meet increasing demand for butadiene.

In addition, according to the method of preparing butadiene by oxidative dehydrogenation of butene, in addition to raw materials, nitrogen, steam, or the like is added as a diluent gas for the purpose of reducing explosion risk due to oxygen and for removal of heat of reaction. When hydrocarbons are isolated from reaction products including diluent gases, light gas species (COx, $O_2$, and the like), hydrocarbons, and the like, a method of absorbing hydrocarbons from reaction products and a method of liquefying hydrocarbons by cooling reaction products may be used. Thereamong, the absorption method is mainly used. In the case of the liquefaction method, a very low-temperature refrigerant is required for liquefaction due to diluent gases, light gas species, and the like present in reaction products. This increases equipment costs, operating costs, and energy consumption, which may lower economic efficiency of processes. For this reason, the absorption method is preferred.

Figure 1:
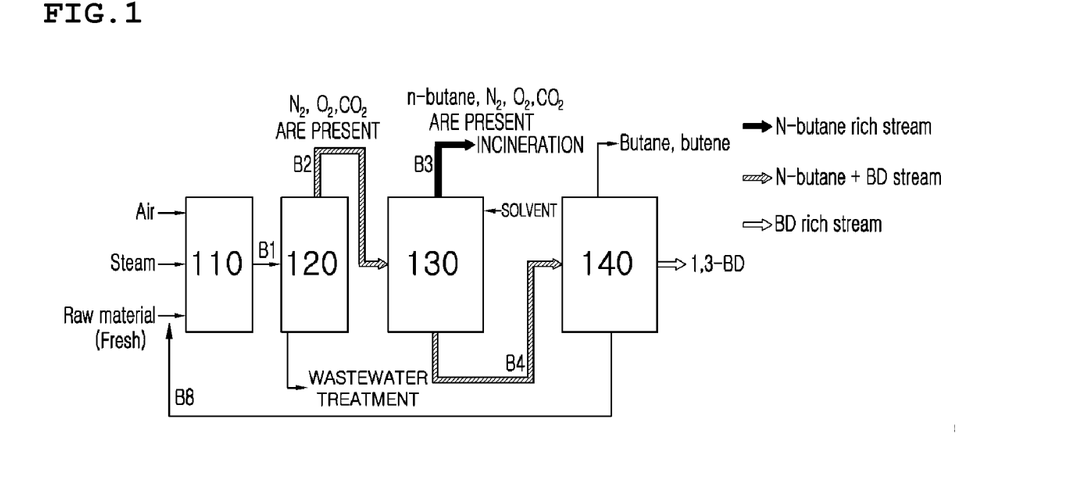
FIG. 1 is a schematic diagram for explaining a conventional device for preparing butadiene and a conventional method of preparing the same.

In this regard, a conventional device for preparing butadiene and a conventional method of preparing the same are described in FIG. 1.

Referring to FIG. 1, the conventional device includes an oxidative dehydrogenation reaction part 110 responsible for producing reaction products containing butadiene from reaction raw materials including butene, oxygen ($O_2$), steam, and a diluent gas (nitrogen); a cooling separation part 120 responsible for removing water from the reaction products obtained by oxidative dehydrogenation; an absorption separation part 130 responsible for separating butadiene or a C4 mixture containing butadiene, and hydrocarbons from the oxidative dehydrogenation reaction products, from which water is removed; and a purification part 140 responsible for purifying butadiene from the butadiene-containing stream separated in the absorption separation part 130.

The oxidative dehydrogenation reaction part 110 may be operated to react reaction raw materials including butene, oxygen ($O_2$), steam, a diluent gas ($N_2$), and unreacted butene recovered in the purification part in the presence of a ferrite catalyst or a bismuth molybdate catalyst under isothermal or adiabatic conditions.

The cooling separation part 120 may be operated by a quenching-type direct cooling system (quencher) or an indirect cooling system.

FIG. 1 shows an example of selectively absorbing and separating only butadiene in the absorption separation part 130. However, in the absorption separation part 130, only butadiene may be selectively absorbed from reaction products from which water is removed, or all hydrocarbons including a C4 mixture may be absorbed using a solvent. Specific examples of solvents capable of selectively absorbing butadiene may include acetonitrile (ACN), N-methylpyrrolidone (NMP), dimethyl formamide (DMF), and the like, and specific examples of solvents capable of absorbing all hydrocarbons including a C4 mixture may include toluene, xylene, and the like. In the absorption separation part 130, COx, $O_2$, and $N_2$ used as a diluent gas are all incinerated, or in some cases, a portion thereof is recovered in the reaction part and reused, and the remainder is incinerated.

For example, the purification part 140 is conventional butadiene purification equipment. In the purification part 140, an acetonitrile (ACN) process, a N-methylpyrrolidone (NMP) process, or a dimethyl formamide (DMF) process may be performed. When necessary, parts of these processes may be performed in modified form to purify butadiene.

However, in general, an excess of a solvent is used in an absorption separation process. Thus, a large amount of energy is consumed in the process of recovering an absorption solvent and the process of recovering and purifying butadiene in the purification part 140. Alternatively, when the absorption separation process is replaced by a condensation process, a very low-temperature refrigerant is required. In this case, energy consumption, raw material costs, and production costs are increased, thereby lowering economic efficiency of processes. Therefore, there is an urgent need to develop related technologies to solve these problems.

PRIOR ART DOCUMENT

[Patent Document] (Patent Document 1) KR 10-2012-0103759 A.

DISCLOSURE

Technical Problem

Therefore, the present invention has been made in view of the above problems, and it is one object of the present invention to provide a method of preparing butadiene. According to the method of the present invention, when butadiene is prepared by oxidative dehydrogenation of butene, unlike conventional methods, in which nitrogen is used as a diluent gas and an absorption method is used to separate butadiene from oxidative dehydrogenation reaction products, butane is used as a diluent gas and a condensation method, in which butadiene is liquefied and separated from oxidative dehydrogenation reaction products using a low-temperature refrigerant or cooling water, is used. In particular, to minimize loss of active ingredients (all hydrocarbons including butadiene) discharged with a stream including $CO_x$, $O_2$, n-butane, and the like separated in a condensation process, a method of recovering all active ingredients from an upper stream generated in the condensation process is used.

The above and other objects can be accomplished by the present disclosure described below.

Technical Solution

In accordance with one aspect of the present invention, provided is a method of preparing butadiene, including a step of obtaining oxidative dehydrogenation reaction products containing butadiene, which are generated when reaction raw materials containing butene, oxygen ($O_2$), steam, and a diluent gas are passed through an oxidative dehydrogenation reaction part;

a step of removing water from the oxidative dehydrogenation reaction products containing butadiene by passing the oxidative dehydrogenation reaction products through a cooling separation part;

a step of condensing hydrocarbons by passing the oxidative dehydrogenation reaction products, from which water is removed, through a condensation separation part;

a step of recovering all hydrocarbons not condensed in the condensation separation part by passing oxidative dehydrogenation reaction products containing hydrocarbons not condensed in the condensation separation part through an absorption separation part; and a step of separating butadiene by passing crude hydrocarbons including n-butane, butene, butadiene, and the like, which are condensed in the condensation separation part, and crude hydrocarbons including n-butane, butene, butadiene, and the like, which are recovered in the absorption separation part, through a purification part, wherein n-butane and butene excluding butadiene, which are separated in the purification part, are fed again into the oxidative dehydrogenation reaction part, and the diluent gas is butane.

In accordance with another aspect of the present invention, provided is a device for preparing butadiene, including an oxidative dehydrogenation reaction part, in which oxidative dehydrogenation of reaction raw materials containing butene, oxygen ($O_2$), steam, and a diluent gas is performed to obtain oxidative dehydrogenation reaction products containing butadiene;

a cooling separation part responsible for removing water from the oxidative dehydrogenation reaction products resulting from oxidative dehydrogenation;

a condensation separation part responsible for condensing hydrocarbons from the oxidative dehydrogenation reaction products, from which water is removed;

an absorption separation part responsible for recovering all hydrocarbons from oxidative dehydrogenation reaction products containing hydrocarbons not condensed in the condensation separation part; and a purification part responsible for separating butadiene from crude hydrocarbons including n-butane, butene, butadiene, and the like, which are condensed in the condensation separation part, and crude hydrocarbons including n-butane, butene, butadiene, and the like, which are recovered in the absorption separation part, wherein n-butane and butene excluding butadiene, which are separated in the purification part, are fed again into the oxidative dehydrogenation reaction part, and the diluent gas is butane.

Advantageous Effects

As apparent from the foregoing, the present invention advantageously provides a method of preparing butadiene. According to the present invention, when butadiene is prepared by oxidative dehydrogenation of butene, unlike conventional methods, in which nitrogen is used as a diluent gas and an absorption method is used to separate butadiene from oxidative dehydrogenation reaction products, butane is used as a diluent gas and a condensation method, in which butadiene is liquefied and separated from oxidative dehydrogenation reaction products using a low-temperature refrigerant or cooling water, is used. In addition, an absorption method of recovering all hydrocarbons from an upper stream generated in a condensation process is used, so that loss of hydrocarbons is minimized. Therefore, the method of the present invention can reduce energy consumption, raw material costs, and production costs, thereby improving economic efficiency of processes.

BEST MODE

Hereinafter, the method of preparing butadiene and the device for preparing the same according to the present invention will be described in detail. According to the present invention, butane is used as a diluent gas when a condensation separation process is performed, and an absorption separation process, in which all active ingredients contained in a stream discharged to the outside through the upper portion of a condensation separation part are recovered, is employed. In the case that butane is used as a diluent gas as described above, in the condensation separation process, hydrocarbons may be easily separated from oxidative dehydrogenation reaction products using a low-temperature refrigerant or cooling water, and in an absorption separation part, all hydrocarbons discharged to the outside are recovered to minimize loss of active ingredients discharged to the outside of the system. Thus, when the method and device of the present invention are used, high-purity butadiene may be prepared while reducing production costs.

The method of preparing butadiene and the device for preparing the same according to the present invention will be described in detail with reference to the accompanying drawings. FIGS. 2 to 6 are schematic diagrams for explaining the device for preparing butadiene and the method of preparing the same according to the present invention.

Figure 2:
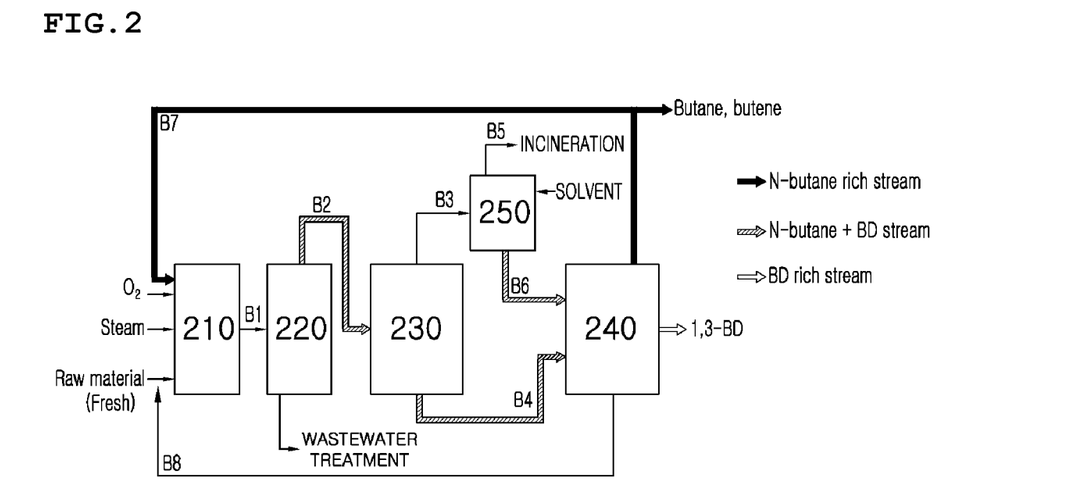
FIGS. 2 to 6 are schematic diagrams for explaining the device for preparing butadiene and the method of preparing the same according to the present invention.

Referring to FIG. 2, first, reaction raw materials containing butene, oxygen ($O_2$), steam, and a diluent gas (butane) are passed through an oxidative dehydrogenation reaction part 210 to obtain oxidative dehydrogenation reaction products containing butadiene. In this case, raw materials used for oxidative dehydrogenation may be combined with discharge streams B7 and B8 resulting from a purification process and introduced into the oxidative dehydrogenation reaction part 210, and a stream B1 resulting from the reaction process may include butadiene, n-butane, butene, $O_2$, COx, $H_2O$, and the like. The discharge stream B1 generated in the oxidative dehydrogenation reaction part 210 is introduced into a cooling separation part 220 and water is separated therein.

A discharge stream B2 generated after the cooling separation process may contain butadiene, n-butane, butene, $O_2$, COx, and the like, and the discharge stream B2 is introduced into a condensation separation part 230.

A discharge stream B3 generated after the condensation separation process may contain oxidative dehydrogenation reaction products containing hydrocarbons, which are not condensed after condensation of hydrocarbons is performed using cooling water, and the like according to a compression/cooling manner in the condensation separation part. The discharge stream B3 may be introduced into an absorption separation part 250, and hydrocarbons may be recovered.

Another discharge stream B4 generated after the condensation separation process may contain crude hydrocarbons including n-butane, butene, and butadiene, which are condensed in the condensation separation part 230. The discharge stream B4 may be introduced into a purification part 240, and butadiene may be purified.

A discharge stream B5 generated after the absorption separation process may contain $O_2$, COx, and the like, which are separated in the previous condensation separation process, and another discharge stream B6 generated after the absorption separation process may contain crude hydrocarbons including n-butane, butene, butadiene, and the like excluding COx and $O_2$, which are separated in the absorption separation part 250. Butadiene may be separated by passing the discharge streams B6 through the purification part 240.

A discharge stream B7 generated after the purification process may contain a large amount of residual n-butane, and a recirculation stream, in which the stream B7 is fed again into the oxidative dehydrogenation reaction part 210, may be formed. A discharge stream B8 containing butene remaining after butadiene is separated in the purification part 240 may be fed again into the oxidative dehydrogenation reaction part 210, thereby forming a recirculation stream.

The term "crude hydrocarbons" refers to crude hydrocarbons commonly used in the art to which the present invention pertains. Unless otherwise specified herein, the crude hydrocarbons refer to hydrocarbons including butadiene and the like recovered from oxidative dehydrogenation reaction products, and are used as raw materials in the purification part.

The term "COx" refers to CO and $CO_2$ unless otherwise specified herein.

In the present invention, butene may be 1-butene, 2-butene, or a mixture thereof. Raw materials containing butene generally used to prepare butadiene are not particularly limited and may be used as the raw materials containing butene of the present invention.

For example, butene may be obtained from a hydrocarbon mixture including butenes, such as raffinate-2 and raffinate-3, included in the C4 fraction produced when high-purity butene and naphtha are decomposed.

The steam is a gas which is injected for the purpose of preventing coking of a catalyst and removing heat of reaction while reducing risk of explosion of reactants when oxidative dehydrogenation is performed.

In the present invention, oxygen ($O_2$) reacts with butene as an oxidizing agent to cause dehydrogenation.

Any catalysts may be used as the catalyst of the present invention packed in the reactor without any particular limitation as long as the catalysts are capable of catalyzing oxidative dehydrogenation of butene to prepare butadiene. For example, ferrite catalysts or bismuth molybdate catalysts may be included.

In one embodiment of the present invention, the catalyst may be a ferrite catalyst. In particular, when zinc ferrite, magnesium ferrite, or manganese ferrite is used, selectivity for butadiene may be increased. The kind and amount of the reaction catalyst may vary depending on specific reaction conditions.

The diluent gas may be butane.

For example, the oxidative dehydrogenation reaction part 210 may be operated under isothermal or adiabatic conditions, in which case freshly supplied butene, oxygen ($O_2$), steam, re-supplied n-butane and butene are used as reaction raw materials, and a ferrite catalyst is used as a catalyst, wherein re-supplied n-butane and butene are residues remaining after butadiene is separated in the purification part 240 and are fed again into the oxidative dehydrogenation reaction part.

For example, oxygen ($O_2$) contained in the reaction raw materials may be fed in a gaseous form having a purity of 90% or more, 95% or more, or 95% or more.

Feeding of oxygen ($O_2$) in a gaseous form having a purity of 90% or more refers that oxygen is not supplied from air, but is fed in a pure oxygen form. Thus, by measuring the amount of active ingredients in real time, it is possible to control the amount of each of components contained in reaction raw materials fed into a reactor.

For example, in the oxidative dehydrogenation reaction part 210, oxidative dehydrogenation may be performed in a molar ratio of butene:oxygen:steam:diluent gas (n-butane)=1:0.5 to 3:0.1 to 20:0.1 to 20. Within this range, energy consumption and raw material costs may be reduced, and productivity may be improved, thereby increasing economic efficiency of processes.

As a particular example, the oxidative dehydrogenation reaction part 210 is preferably operated in a molar ratio of oxygen:butene=0.5 to 3:1, a molar ratio of steam:butene=1 to 20:1, and a molar ratio of n-butane:butene=0.1 to 20:1 at a reaction pressure of atmospheric pressure to 10 atm and a reaction temperature of 150 to 650° C. under isothermal or adiabatic conditions. Within this range, energy consumption and raw material costs may be reduced, and productivity may be improved, thereby increasing economic efficiency of processes.

For example, the cooling separation part 220 may be operated by a quenching-type direct cooling system (quencher) or an indirect cooling system. In this case, the cooling separation part may be rapidly cooled to a temperature of 0 to 100° C.

For example, the condensation separation part 230 may have a single-stage compression structure having one stage or a multistage compression structure having 1 to 10 stages or 1 to 2 stages. When compressing from an initial pressure to a target pressure at a time, a lot of power is required. In addition, heat is generated due to gas compression, which causes gas expansion, resulting in poor compression efficiency. Therefore, to prevent such problems, multi-stage compression is performed. In this case, heat generated in the compression process may be cooled using a cooler.

In the condensation separation part 230, condensation conditions may be determined so that the stream of the condensation separation part 230 is out of an explosive range in consideration of unreacted oxygen (i.e., above upper explosive limit or below limiting oxygen concentration).

In one embodiment of the present invention, a refrigerant used in the condensation separation part 230 may be one or more selected from the group consisting of cooling water, ethylene glycol, an aqueous solution of ethylene glycol having a concentration of 20 to 100% by weight, propylene glycol, an aqueous solution of propylene glycol having a concentration of 30 to 100% by weigh, and a propylene-based solvent.

For example, the propylene-based solvent, as a compound including propylene or propylene, may have a boiling point of −10° C. or less or −10 to −50° C.

As a particular example, the refrigerant may be cooling water, cooling water having a temperature of 0 to 40° C., or cooling water having a temperature of 5 to 30° C. In this case, the extrusion discharge temperature may be 250° C. or less or 50 to 250° C., and the cooling temperature of a compression discharge stream may be 120° C. or less or 20 to 80° C.

Conventionally, since nitrogen is used as a diluent gas, a very low-temperature refrigerant is required when a dilution gas and light gas species are separated using a condensation method. In the present invention, since butane is used as a diluent gas, a lower grade of refrigerant may be used.

For example, a conventional apparatus for purifying butadiene may be used as the purification part 240. For example, in the purification part 240, an acetonitrile (ACN) process, a N-methylpyrrolidone (NMP) process, or a dimethyl formamide (DMF) process may be performed.

For example, the absorption separation part 250 may be operated in an absorption manner, in which toluene, xylene, or the like is used as a solvent for absorbing all hydrocarbons.

In a purification step, solvents, high boiling point components and low boiling point components are removed from reaction products containing butadiene obtained in the separation step, and thus high-purity butadiene may be obtained.

In one embodiment of the present invention, the purity of finally obtained butadiene through the series of steps described above may be 95.0 to 99.9%.

Figure 3:
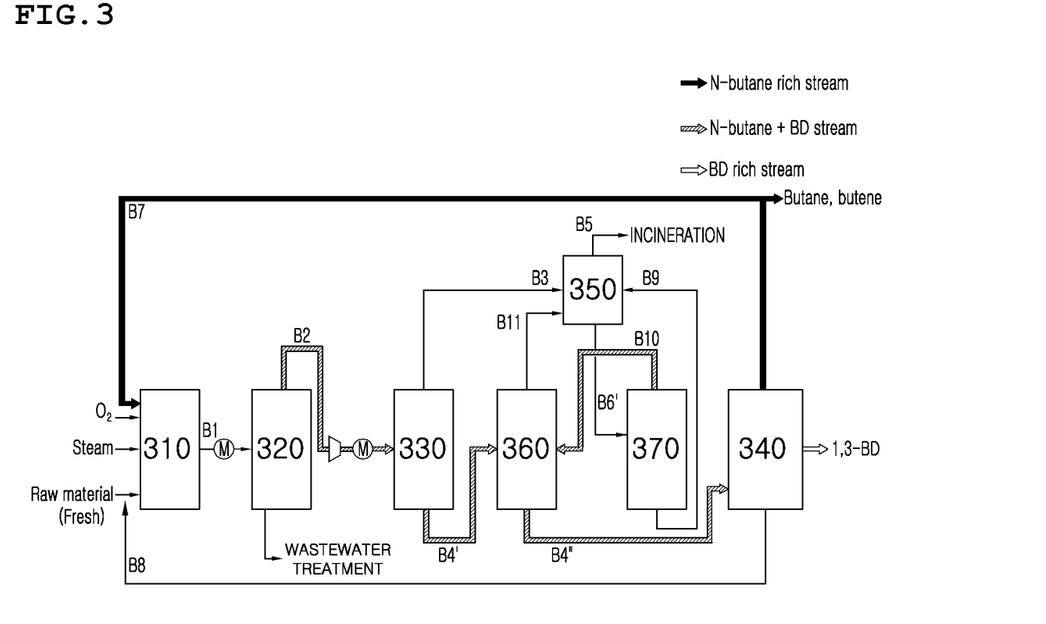

FIG. 3 is a schematic diagram showing a process, in which oxidative dehydrogenation reaction products, from which water is removed in the cooling separation part 220 as shown in FIG. 2, are fed into a purification part 240 (via streams B4 and B6) through the condensation separation part 230 and the absorption separation part 250. At this time, the process is explained including a degasification part and a solvent recovery part.

For example, the degasification part and the solvent recovery part may be operated by stripping using a conventional column, or degasification.

Referring to FIG. 3, first, oxidative dehydrogenation reaction products containing butadiene are obtained by passing reaction raw materials containing butene, oxygen ($O_2$), steam, and a diluent gas (butane) through an oxidative dehydrogenation reaction part 310. At this time, raw materials for oxidative dehydrogenation may be combined with the discharge streams B7 and B8 generated after the purification process, and introduced into the oxidative dehydrogenation reaction part 310. The stream B1 resulting from the reaction process may include butadiene, n-butane, butene, $O_2$, COx, $H_2O$, and the like.

The stream B1 discharged from the oxidative dehydrogenation reaction part 310 is introduced into a cooling separation part 320, and water is removed from the stream B1.

The discharge stream B2 generated after the cooling separation process may contain butadiene, n-butane, butene, $O_2$, COx, and the like. The discharge stream B2 is introduced into the condensation separation part, and hydrocarbons are condensed.

The discharge stream B3 generated after the condensation separation process may contain oxidative dehydrogenation reaction products containing hydrocarbons not condensed when hydrocarbons are condensed using cooling water through compression/cooling in the condensation separation process. The discharge stream B3 is introduced into an absorption separation part 350.

The discharge stream B5 generated after the absorption separation process may contain $O_2$, COx, and the like, which are separated in the previous condensation separation process. A discharge stream B6' generated after the absorption separation process may contain a solvent, in which hydrocarbons including n-butane, butene, butadiene, and the like excluding COx and $O_2$, which are generated in the absorption separation part 350, are absorbed. The discharge stream B6' may be introduced into a solvent recovery part 370 to recover the solvent, and the recovered solvent may be fed again into the absorption separation part 350 through a discharge stream B9.

Another discharge stream B10 generated after the solvent is recovered and a discharge stream B4' containing hydrocarbons condensed in a condensation separation part 330 may be introduced into a degasification part 360 to additionally separate COx and $O_2$.

A discharge stream B11 generated after the degasification process may contain COx and $O_2$ additionally separated in the degasification part 360, and may be introduced into the absorption separation part 350 and an absorption separation process may be performed. Another discharge stream B4″ generated after the degasification process may contain crude hydrocarbons including n-butane, butene, and butadiene excluding COx and $O_2$, which are additionally separated in the degasification part 360, and may be introduced into a purification part 340 to separate butadiene.

The discharge stream B7 generated after the purification process may contain a large amount of residual n-butane, and a recirculation stream, in which the discharge stream B7 is introduced into the oxidative dehydrogenation reaction part 310, may be formed.

The discharge stream B8 containing butene remaining after butadiene is separated in the purification part 340 may be mixed with butene supplied as a raw material, and form a recirculation stream, in which the stream is introduced into the oxidative dehydrogenation reaction part 310.

Figure 4:
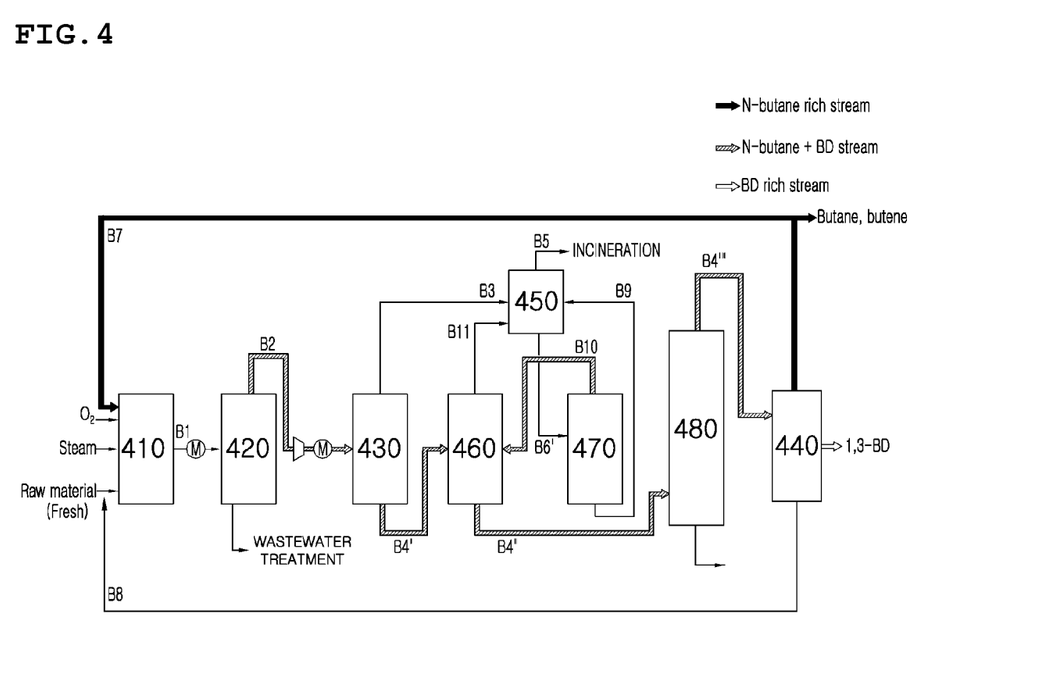

FIG. 4 is a schematic diagram showing a process, in which another discharge stream B4‴ is additionally added to the discharge stream B4″ generated after the degasification process in FIG. 3. The discharge stream B4″ may contain crude hydrocarbons including n-butane, butene, butadiene, high-boiling point materials, and the like excluding COx and $O_2$, which are additionally separated in a degasification part 460. The discharge stream B4‴, in which high-boiling point materials are separated in a high-boiling point material removal part 480, may include crude hydrocarbons including n-butane, butene, butadiene, and the like, from which high-boiling point materials are removed, and may be purified in a purification part 440.

For example, the high-boiling point material removal part 480 may be operated according to a distillation method.

For example, the high-boiling point materials may be aromatic hydrocarbons, such as benzene, styrene, and phenol, butadiene dimers, acetophenone, benzophenone, or anthraquinone.

Referring to FIG. 4, first, reaction raw materials containing butene, oxygen ($O_2$), steam, and a diluent gas (butane) are passed through an oxidative dehydrogenation reaction part 410 to obtain oxidative dehydrogenation reaction products containing butadiene. At this time, raw materials for oxidative dehydrogenation may be combined with the discharge streams B7 and B8 generated after the purification process, and introduced into the oxidative dehydrogenation reaction part 410. The stream B1 discharged after the process may contain butadiene, n-butane, butene, $O_2$, COx, $H_2O$, and the like. The stream B1 discharged from the oxidative dehydrogenation reaction part 410 is introduced into a cooling separation part 420, and water is removed.

AS in FIG. 3, the discharge stream B2 generated after the cooling separation process may contain butadiene, n-butane, butene, $O_2$, COx, and the like, and may be introduced into a condensation separation part 430.

The discharge stream B3 generated after the condensation separation process may contain oxidative dehydrogenation reaction products containing hydrocarbons not condensed when hydrocarbons are condensed using cooling water through compression/cooling in the condensation separation process, and may be introduced into an absorption separation part 450.

The discharge stream B5 generated after the absorption separation process may contain $O_2$, COx, and the like, which are separated in the previous condensation separation process. The discharge stream B6' generated after the absorption separation process may contain a solvent, in which hydrocarbons including n-butane, butene, butadiene, and the like excluding COx and $O_2$ are absorbed in the absorption separation part 450. The discharge stream B6' may be passed through a solvent recovery part 470 to recover the solvent, and the recovered solvent may be fed again into the absorption separation part 450 through the discharge stream B9.

Another discharge stream B10 generated after the solvent is recovered and the discharge stream B4' containing hydrocarbons condensed in the condensation separation part 430 may be passed through the degasification part 460 to additionally separate COx and $O_2$.

The discharge stream B11 generated after the degasification process may contain COx and $O_2$ additionally separated in the degasification part 460. The discharge stream B11 may be fed into the absorption separation part 450, and absorption separation may be performed. Another discharge stream B4''' generated after the degasification process may contain crude hydrocarbons including n-butane, butene, and butadiene, high-boiling point materials, and the like excluding COx and $O_2$, which are additionally separated in the degasification part 460, and may be introduced into the high-boiling point material removal part 480, and high-boiling point materials are removed.

For example, the high-boiling point materials may be aromatic hydrocarbons, such as benzene, styrene, and phenol, butadiene dimers, acetophenone, benzophenone, or anthraquinone.

The discharge stream B4'''' generated after the high-boiling point materials are removed may contain crude hydrocarbons including n-butane, butene, butadiene, and the like, from which high-boiling point materials are removed, and may be fed into the purification part 440 to separate butadiene.

The discharge stream B7 generated after the purification process may contain a large amount of residual n-butane. A recirculation stream, in which the discharge stream B7 is introduced into the oxidative dehydrogenation reaction part 410, may be formed.

The discharge stream B8 containing residual butene remaining after butadiene is separated in the purification part 440 may be combined with butene supplied as a raw material and fed into the oxidative dehydrogenation reaction part 410, resulting in formation of a recirculation stream.

Figure 5:
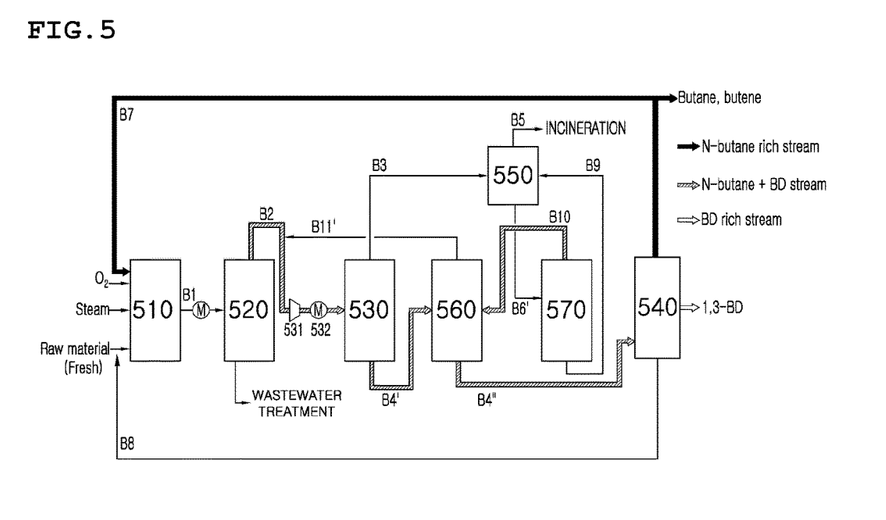

FIG. 5 is a schematic diagram showing a case where the discharge stream B11 generated after the degasification process in FIG. 3 is replaced with another discharge stream B11'. In this case, gas separation efficiency may be improved by feeding COx and $O_2$ separated in a degasification part 560 into the condensation system.

Unless otherwise specified herein, the condensation system refers to a system including a compressor 531, a heat exchanger 532, and a condensation separation part 530.

Referring to FIG. 5, first, reaction raw materials containing butene, oxygen ($O_2$), steam, and a diluent gas (butane) are passed through an oxidative dehydrogenation reaction part 510 to obtain oxidative dehydrogenation reaction products containing butadiene. At this time, raw materials for oxidative dehydrogenation may be combined with the discharge streams B7 and B8 generated after the purification process, and introduced into the oxidative dehydrogenation reaction part 510. The stream B1 discharged after the process may contain butadiene, n-butane, butene, $O_2$, COx, $H_2O$, and the like. The stream B1 discharged from the reaction part is introduced into a cooling separation part 520, and water is removed.

The discharge stream B2 generated after the cooling separation process may contain butadiene, n-butane, butene, $O_2$, COx, and the like, and may be introduced into the condensation separation part.

The discharge stream B3 generated after the condensation separation process may contain oxidative dehydrogenation reaction products containing hydrocarbons not condensed when hydrocarbons are condensed using cooling water through compression/cooling in the condensation separation process. The discharge stream B3 may be introduced into an absorption separation part 550.

The discharge stream B5 generated after the absorption separation process may contain $O_2$, COx, and the like, which are separated in the previous condensation separation process. Another discharge stream B6' generated after the absorption separation process may contain a solvent, in which hydrocarbons including n-butane, butene, butadiene, and the like excluding COx and $O_2$ are absorbed in the absorption separation part 550. The discharge stream B6' may be passed through a solvent recovery part 570 to recover the solvent, and the recovered solvent may be fed again into the absorption separation part 550 through the discharge stream B9.

Another discharge stream B10 generated after the solvent is recovered, and the discharge stream B4' containing hydrocarbons condensed in the condensation separation part may be passed through the degasification part 560 to additionally separate COx and $O_2$.

The discharge stream B11' generated after the degasification process may contain COx and $O_2$ additionally separated in the degasification part 560. The discharge stream B11' may be introduced into the condensation system, and condensation separation may be performed in the condensation separation part 530. Another discharge stream B4" generated after the degasification process may contain crude hydrocarbons including n-butane, butene, butadiene, and the like excluding COx and $O_2$, which are additionally separated in the degasification part 560. The discharge stream B4" may be fed into a purification part 540 to separate butadiene.

Unless otherwise specified herein, the condensation system refers to a system including the compressor 531 the heat exchanger 532 and the condensation separation part 530.

The discharge stream B7 generated after the purification process may contain a gas containing a large amount of residual n-butane, and form a recirculation stream, in which the discharge stream B7 is introduced into the oxidative dehydrogenation reaction part 510. The discharge stream B8 containing residual butene remaining after butadiene is separated in the purification part 540 may be combined with butene supplied as a raw material, and introduced into the oxidative dehydrogenation reaction part 510, resulting in formation of a recirculation stream.

Figure 6:
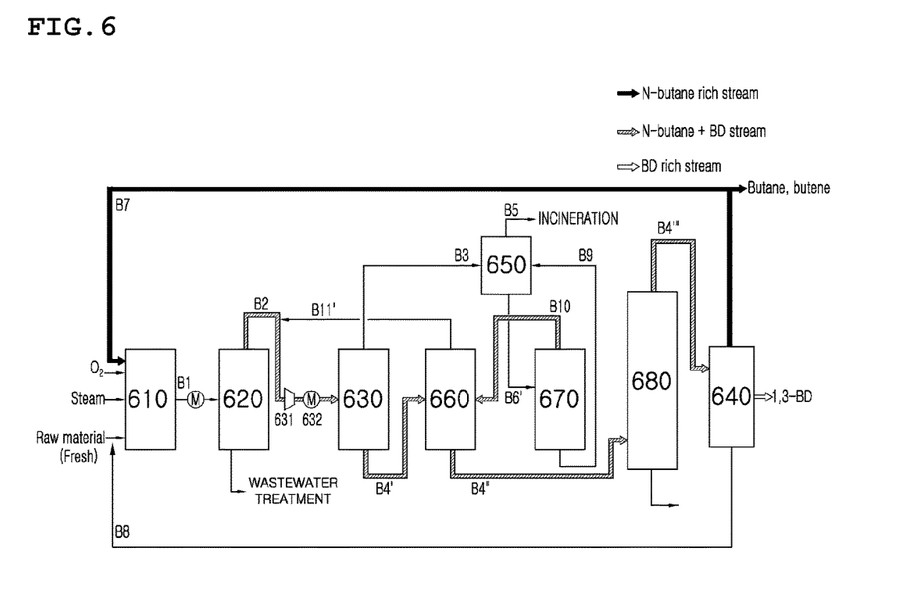

FIG. 6 is a schematic diagram showing a case where the discharge stream B11 generated after the degasification process in FIG. 4 is replaced with another discharge stream B11'. In this case, when COx and $O_2$ separated in a degasification part 660 are fed into the condensation system, COx and $O_2$ are circulated to a condensation separation part 630, thereby improving gas separation efficiency.

Referring to FIG. 6, first, reaction raw materials containing butene, oxygen ($O_2$), steam, and a diluent gas (butane) are passed through an oxidative dehydrogenation reaction part 610 to obtain oxidative dehydrogenation reaction products containing butadiene. At this time, raw materials for oxidative dehydrogenation may be combined with the discharge streams B7 and B8 generated after the purification process, and introduced into the oxidative dehydrogenation reaction part 610. The stream B1 discharged after the process may contain butadiene, n-butane, butene, $O_2$, COx, $H_2O$, and the like. The discharge stream B1 generated after the reaction process is introduced into a cooling separation part 620.

As in FIG. 5, the discharge stream B2 generated after the cooling separation process may contain butadiene, n-butane, butene, $O_2$, COx, and the like, and introduced into the condensation separation part.

The discharge stream B3 generated after the condensation separation process may contain oxidative dehydrogenation reaction products containing hydrocarbons not condensed when hydrocarbons are condensed using cooling water through compression/cooling in the condensation separation process. The discharge stream B3 is introduced into an absorption separation part 650.

The discharge stream B5 generated after the absorption separation process may contain $O_2$, COx, and the like, which are not separated in the previous condensation separation process. Another discharge stream B6' generated after the absorption separation process may contain a solvent, in which hydrocarbons including n-butane, butene, butadiene, and the like excluding COx and $O_2$, which are separated in the absorption separation part 650, are absorbed. The discharge stream B6' may be passed through a solvent recovery part 670 to recover the solvent, and the recovered solvent may be fed again into the absorption separation part 650 through the discharge stream B9.

Another discharge stream B10 generated after the solvent is recovered, and the discharge stream B4' containing hydrocarbons condensed in the condensation separation part 630 may be passed through the degasification part 660 to additionally separate COx and $O_2$.

The discharge stream B11' generated after the degasification process may contain COx and $O_2$ additionally separated in the degasification part 660. The discharge stream B11' may be fed into the condensation system, and recondensation may be performed therein.

Unless otherwise specified herein, the condensation system refers to a system including a compressor 631, a heat exchanger 632, and the condensation separation part 630.

Another discharge stream B4" generated after the degasification process may contain crude hydrocarbons including butane, butene, butadiene, high-boiling point materials, and the like excluding COx and $O_2$, which are additionally separated in the degasification part 660. The discharge stream B4" is introduced into a high-boiling point material removal part 680, and high-boiling point materials are separated. The discharge stream B4''' generated in the high boiling point removal process may contain crude hydrocarbons including n-butane, butene, butadiene, and the like, from which high-boiling point materials are removed, and fed into a purification part 640 to separate butadiene.

The discharge stream B7 generated after the purification process may contain a large amount of residual n-butane, and form a recirculation stream, in which the discharge stream B7 is fed into the oxidative dehydrogenation reaction part 610. The discharge stream B8 containing residual butene remaining after butadiene is separated in the purification part 640 may form a recirculation stream, in which the discharge stream B8 is fed into the oxidative dehydrogenation reaction part 610.

For example, a device used in the method of the present invention, referring to FIG. 2, includes the oxidative dehydrogenation reaction part 210, in which oxidative dehydrogenation of reaction raw materials containing butene, oxygen ($O_2$), steam, and a diluent gas (butane) is performed to obtain oxidative dehydrogenation reaction products containing butadiene; a cooling separation part 220 responsible for removing water from the oxidative dehydrogenation reaction products containing butadiene; the condensation separation part 230 responsible for condensing hydrocarbons from the oxidative dehydrogenation reaction products, from which water is removed; the absorption separation part 250 responsible for recovering all hydrocarbons from oxidative dehydrogenation reaction products containing hydrocarbons not condensed in the condensation separation part 230; and the purification part 240 responsible for separating butadiene from a discharge stream containing crude hydrocarbons including n-butane, butene, butadiene, and the like, which are condensed in the condensation separation part 230, wherein the device is configured so that the discharge stream B7 containing n-butane excluding butadiene separated in the purification part 240 is fed again into the oxidative dehydrogenation reaction part 210.

The device is configured so that the discharge stream B6 containing crude hydrocarbons including n-butane, butene, butadiene, and the like, which are recovered in the absorption separation part 250, is fed into the purification part 240.

The device is configured so that the discharge stream B8 containing butene remaining after butadiene is separated in the purification part 240 is fed again into the oxidative dehydrogenation reaction part 210.

As another example, a device for preparing butadiene, referring to FIG. 3, includes the oxidative dehydrogenation reaction part 310, in which oxidative dehydrogenation of reaction raw materials containing butene, oxygen ($O_2$), steam, and a diluent gas (butane) is performed to obtain oxidative dehydrogenation reaction products containing butadiene; a cooling separation part 320 responsible for removing water from the oxidative dehydrogenation reaction products containing butadiene; the condensation separation part 330 responsible for condensing hydrocarbons from the oxidative dehydrogenation reaction products, from which water is removed; and the absorption separation part 350 responsible for recovering all hydrocarbons from oxidative dehydrogenation reaction products containing hydrocarbons not condensed in the condensation separation part 330.

The device is configured so that the discharge stream B6' containing hydrocarbons including n-butane, butene, butadiene, and the like, which are recovered in the absorption separation part 350, is fed into the solvent recovery part 370 responsible for recovering a solvent, and the discharge stream B9 containing the solvent recovered in the solvent recovery part 370 is recycled to the absorption separation part 350.

Preferably, the device further includes the degasification part 360 responsible for separating COx, $O_2$, hydrocarbons including n-butane, butene, butadiene, and the like from the discharge stream B4' consisting of hydrocarbons including n-butane, butene, butadiene, and the like, which are condensed in the condensation separation part 330, and the discharge stream B10 consisting of hydrocarbons including n-butane, butene, butadiene, and the like, from which the solvent is removed in the solvent recovery part 370.

The device is configured so that the discharge stream B11 containing COx and $O_2$ separated in the degasification part 360 is introduced into the absorption separation part 350.

The device is configured so that the discharge stream B4" containing crude hydrocarbons including n-butane, butene, butadiene, and the like excluding COx and $O_2$, which are separated in the degasification part 360, is fed into the purification part 340.

The device further includes the purification part 340 for separating butadiene, and is configured so that the discharge stream B7 containing n-butane excluding butadiene separated in the purification part 340 is fed again into the oxidative dehydrogenation reaction part 310. In addition, the device is configured so that the discharge stream B8 containing butene remaining after butadiene is separated in the purification part 340 is combined with butene supplied as a raw material and fed again into the oxidative dehydrogenation reaction part 310.

As another example, a device for preparing butadiene, referring to FIG. 4, includes the oxidative dehydrogenation reaction part 410, in which oxidative dehydrogenation of reaction raw materials containing butene, oxygen ($O_2$), steam, and a diluent gas (butane) is performed to obtain oxidative dehydrogenation reaction products containing butadiene; a cooling separation part 420 responsible for removing water from the oxidative dehydrogenation reaction products containing butadiene; the condensation separation part 430 responsible for condensing hydrocarbons from the oxidative dehydrogenation reaction products, from which water is removed; and the absorption separation part 450 responsible for recovering all hydrocarbons from oxidative dehydrogenation reaction products containing hydrocarbons not condensed in the condensation separation part 430.

The device is configured so that the discharge stream B6' containing hydrocarbons including n-butane, butene, butadiene, and the like, which are recovered in the absorption separation part 450, is fed into the solvent recovery part 470 responsible for recovering the solvent, and the discharge stream B9 containing the solvent recovered in the solvent recovery part 470 is recycled to the absorption separation part 450.

Preferably, the device further includes the degasification part 460 responsible for separating COx, $O_2$, hydrocarbons including n-butane, butene, butadiene, and the like from the discharge stream B4' consisting of hydrocarbons including n-butane, butene, butadiene, and the like, which are condensed in a condensation separation part 420, and the discharge stream B10 consisting of hydrocarbons including n-butane, butene, butadiene, and the like, from which the solvent is removed in the solvent recovery part 470.

The device is configured so that the discharge stream B11 containing COx and $O_2$ separated in the degasification part 460 is introduced into the absorption separation part 450.

The device is configured so that the discharge stream B4" containing crude hydrocarbons including n-butane, butene, butadiene, high-boiling point materials, and the like excluding COx and $O_2$, which are separated in the degasification part 460, is fed into the high-boiling point material removal part 480 to remove high-boiling point materials, and the discharge stream B4'" containing crude hydrocarbons including n-butane, butene, butadiene, and the like, which are separated in the high-boiling point material removal part 480, is fed into the purification part 440.

The device further includes the purification part 440 responsible for separating butadiene, and is configured so that the discharge stream B7 containing n-butane excluding butadiene separated in the purification part 440 is fed again into the oxidative dehydrogenation reaction part 410.

The device is configured so that the discharge stream B8 containing residual butene remaining after butadiene is separated in the purification part 440 is fed again into the oxidative dehydrogenation reaction part 410.

As another example, a device for preparing butadiene, referring to FIG. 5, includes the oxidative dehydrogenation reaction part 510, in which oxidative dehydrogenation of reaction raw materials containing butene, oxygen ($O_2$), steam, and a diluent gas (butane) is performed to obtain oxidative dehydrogenation reaction products containing butadiene; a cooling separation part 520 responsible for removing water from the oxidative dehydrogenation reaction products containing butadiene; the condensation separation part 530 responsible for condensing hydrocarbons from the oxidative dehydrogenation reaction products, from which water is removed; and the absorption separation part 550 responsible for recovering all hydrocarbons not condensed in the condensation separation part 530.

The device is configured so that the discharge stream B6' containing hydrocarbons including n-butane, butene, butadiene, and the like, which are recovered in the absorption separation part 550, is fed into the solvent recovery part 570 responsible for recovering the solvent, and the discharge stream B9 containing the solvent recovered in the solvent recovery part 570 is recycled to the absorption separation part 550.

Preferably, the device further includes the degasification part 560 responsible for separating COx, $O_2$, and hydrocarbons including n-butane, butene, butadiene, and the like from the discharge stream B4' consisting of hydrocarbons including n-butane, butene, butadiene, and the like, which are condensed in the condensation separation part 530, and the discharge stream B10 consisting of hydrocarbons including n-butane, butene, butadiene, and the like, from which the solvent is removed in the solvent recovery part 570.

The device is configured so that the discharge stream B4" containing crude hydrocarbons including n-butane, butene, butadiene, and the like excluding COx and O₂, which are separated in the degasification part 560, is fed into the purification part 540, and another discharge stream B11' containing COx and O₂ separated in the degasification part 560 is fed into the condensation system.

Unless otherwise specified herein, the condensation system refers to a system including the compressor 531, the heat exchanger 532, and the condensation separation part 530.

The device further includes the purification part 540 responsible for separating butadiene, and is configured so that the discharge stream B7 containing n-butane excluding butadiene separated in the purification part 540 is fed again into the oxidative dehydrogenation reaction part 510. In addition, the device is configured so that the discharge stream B8 containing residual butene remaining after butadiene is separated in the purification part 540 is combined with butene supplied as a raw material, and fed again into the oxidative dehydrogenation reaction part 510.

As another example, a device for preparing butadiene, referring to FIG. 6, includes the oxidative dehydrogenation reaction part 610, in which oxidative dehydrogenation of reaction raw materials containing butene, oxygen (O₂), steam, and a diluent gas (butane) is performed to obtain oxidative dehydrogenation reaction products containing butadiene; a cooling separation part 620 responsible for removing water from the oxidative dehydrogenation reaction products containing butadiene; the condensation separation part 630 responsible for condensing hydrocarbons from the oxidative dehydrogenation reaction products, from which water is removed; and the absorption separation part 650 responsible for recovering all hydrocarbons from oxidative dehydrogenation reaction products containing hydrocarbons not condensed in the condensation separation part 630.

The device is configured so that the discharge stream B6' containing hydrocarbons including n-butane, butene, butadiene, and the like, which are recovered in the absorption separation part 650, is fed into the solvent recovery part 670 responsible for recovering the solvent, and the discharge stream B9 containing the solvent recovered in the solvent recovery part 670 is recycled to the absorption separation part 650.

Preferably, the device further includes the degasification part 660 responsible for separating COx, O₂, and hydrocarbons including n-butane, butene, butadiene, and the like from the discharge stream B4' consisting of hydrocarbons including n-butane, butene, butadiene, and the like, which are condensed in the condensation separation part 630, and the discharge stream B10 consisting of hydrocarbons including n-butane, butene, butadiene, and the like, from which the solvent is removed in the solvent recovery part 670.

The device is configured so that the discharge stream B11' containing COx and O₂ separated in the degasification part 660 is fed into the condensation system.

Unless otherwise specified herein, the condensation system refers to a system including the compressor 631, the heat exchanger 632, and the condensation separation part 630.

The device is configured so that the discharge stream B4" containing crude hydrocarbons including n-butane, butene, butadiene, high-boiling point materials, and the like excluding COx and O₂, which are separated in the degasification part 660, is fed into the high-boiling point material removal part 680 to remove high-boiling point materials, and the discharge stream B4'" containing crude hydrocarbons including n-butane, butene, butadiene, and the like, which are separated in the high-boiling point material removal part 680, is fed into the purification part 640.

The device further includes the purification part 640 responsible for separating butadiene, and is configured so that the discharge stream B7 containing n-butane excluding butadiene separated in the purification part 640 is fed again into the oxidative dehydrogenation reaction part 610. In addition, the device is configured so that the discharge stream B8 containing residual butene remaining after butadiene is separated in the purification part 640 is combined with butene supplied as a raw material and fed again into the oxidative dehydrogenation reaction part 610.

In summary, when the method of preparing butadiene and the device for preparing the same according to the present invention are used, a convention method of preparing butadiene by oxidative dehydrogenation of butene may be used, and butadiene may be separated from reaction products resulting from oxidative dehydrogenation by a liquefaction process using a low-temperature refrigerant or cooling water. As a result, high-purity butadiene may be obtained while reducing the amount of active ingredients discharged to the outside, thereby improving economic efficiency of processes.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLE

Example 1

To obtain oxidative dehydrogenation reaction products containing butadiene, oxidative dehydrogenation of reaction raw materials including butene, steam, and butane in molar ratios of butene:oxygen=1:0.9, butene:steam=1:5, and butene:butane=1:2 was performed under the presence of a ferrite catalyst in the device for preparing butadiene according to FIG. 2. In this case, butane was used as a diluent gas, and raffinate-3 having compositions shown in Table 1 below was used as a butene source. Then, water was removed from the obtained oxidative dehydrogenation reaction products. The water-removed oxidative dehydrogenation reaction products were introduced into a condensation separation part, and pressurized at a compression discharge temperature of 80° C. using a two-stage compressor, and hydrocarbons were condensed at 40° C. using cooling water. Thereafter, to minimize loss of effective hydrocarbons present in the vapor phase of the condensation separation part to the outside, crude hydrocarbons were obtained by absorbing all hydrocarbons using toluene in the absorption separation part. Then, the crude hydrocarbons were fed into the purification part, and purification and recovery processes were performed using DMF as a solvent to obtain butadiene having a final purity of 99.7% by weight.

In this case, the compositions of the discharge streams (B2, B3, B4, B5, B6, B7, B8, final product) of each of the cooling separation part, the condensation separation part, the absorption separation part, and the purification part were calculated using a process stimulator (AspenPlus), and the results are shown in Table 2 below.

In addition, the amounts of the solvent and energy used in the absorption separation part and the purification part are shown in Table 4 and Table 5, respectively. Energy units per mass of butadiene calculated accordance with heat exchange in the butadiene preparation process are shown in Table 6, and the recovery rate and purity of the obtained butadiene are shown in Table 7.

Comparative Example 1

Except that the device for preparing butadiene according to FIG. 1 was used, and nitrogen was used as a diluent gas, experiments were performed in the same manner as in Example 1. As a result, butadiene having a final purity of 99.7% by weight was obtained.

In this case, the compositions of the discharge streams (B2, B3, B4, B5, B6, final product) of each of the cooling separation part, the condensation separation part, the absorption separation part, and the purification part were calculated using a process stimulator (AspenPlus), and the results are shown in Table 3 below.

In addition, the amounts of the solvent and energy used in the absorption separation part and the purification part are shown in Table 4 and Table 5, respectively. Energy units per mass of butadiene calculated accordance with heat exchange in the butadiene preparation process are shown in Table 6, and the recovery rate and purity of the obtained butadiene are shown in Table 7.

TABLE 1

| Composition | % mol | % by weight |
|---|---|---|
| 1-butene | 0.00 | 0.00 |
| Trans-2-butene | 43.20 | 42.77 |
| Cis-2-butene | 28.80 | 28.51 |
| n-butane | 28.00 | 28.72 |

TABLE 2

| | Condensation separation part 230 and absorption separation part 250 | | | | Purification part 240 | | |
|---|---|---|---|---|---|---|---|
| Pressure (kg/cm²g) | 0.3 | 10.9 | 7.0 | 4.5 | 3.7 | 4.5 | 3.7 |
| Temperature (° C.) | 35.0 | 40.0 | 78.5 | 51.2 | 47.4 | 55.6 | 42.1 |

| | Mass flow rate (kg/hr) | | | | | | |
|---|---|---|---|---|---|---|---|
| | B2 | B3 | B5 | B4 + B6 | B7 | B8 | Final product |
| Oxygen | 1,919.4 | 1,836.5 | 1,919.3 | — | — | — | — |
| Nitrogen | — | — | — | — | — | — | — |
| COx | 4,028.0 | 3,181.2 | 4,026.1 | — | — | — | — |
| Water | 4,040.3 | 29.1 | 43.2 | — | — | — | 0.1 |
| Light gases* | 3.3 | 2.0 | 3.3 | — | — | — | — |
| Carbonyl and aldehyde | 59.8 | 3.8 | 18.3 | 40.6 | — | — | — |
| 1-butene | 209.4 | 15.8 | 8.0 | 201.4 | 201.4 | — | 0.0 |
| 1,3-butadiene | 18,741.6 | 1,480.8 | 846.9 | 17,840.5 | 30.3 | 50.0 | 17,639.5 |
| n-butane | 49,250.0 | 3,350.0 | 1,217.4 | 48,032.5 | 48,032.5 | — | — |
| Acetylenes | 22.5 | 2.1 | 2.1 | 20.4 | — | 0.0 | 0.0 |
| Trans-2-butane | 1,786.3 | 117.8 | 28.7 | 1,757.5 | 1,747.0 | 3.6 | 6.9 |
| Cis-2-butane | 609.4 | 37.8 | 6.3 | 603.2 | 293.7 | 261.3 | 47.5 |
| High-boiling point materials** | 137.1 | 0.9 | 115.4 | 75.5 | — | — | — |
| Toluene | — | — | 310.9 | 0.0 | — | — | — |
| DMF | — | — | — | — | 17.8 | — | — |
| Sum | 80,807.1 | 10,057.7 | 8,549.9 | 68,571.7 | 50,322.4 | 314.9 | 17,694.0 |

*Light gas species: gases having lower boiling points than that of the C4 fraction excluding COx and $O_2$.
**High-boiling point materials: aromatic hydrocarbons, such as benzene, styrene, and phenol, butadiene dimers, acetophenone, benzophenone, or anthraquinone

TABLE 3

| | Absorption separation part 130 | | | Purification part 140 | | |
|---|---|---|---|---|---|---|
| Pressure (kg/cm²g) | 3.6 | 3.0 | 4.5 | 3.7 | 4.5 | 3.7 |
| Temperature (° C.) | 40.0 | 46.3 | 48.1 | 47.3 | 54.5 | 42.1 |

TABLE 3-continued

| | Mass flow rate (kg/hr) | | | | | |
|---|---|---|---|---|---|---|
| | B2 | B3 | B4 | B5 | B6 | Final product |
| Oxygen | 2,720.3 | 2,720.3 | — | — | — | — |
| Nitrogen | 19,018.1 | 19,018.1 | — | — | — | — |
| COx | 4,025.5 | 4,025.5 | 0.0 | 0.0 | — | — |
| Water | 447.6 | 212.9 | 234.8 | — | — | 0.2 |
| Light gases* | 3.3 | 3.3 | — | — | — | — |
| Carbonyl and aldehyde | 59.2 | 29.7 | 26.5 | — | — | — |
| 1-butene | 209.4 | 32.2 | 177.2 | 177.2 | — | — |
| 1,3-butadiene | 18,736.2 | 1,376.3 | 17,359.6 | 30.0 | 50.0 | 17,140.6 |
| n-butane | 9,573.7 | 1,768.8 | 7,804.8 | 7,804.8 | — | — |
| Acetylenes | 22.5 | 0.1 | 22.4 | — | — | — |
| Trans-2-butane | 1,785.8 | 107.7 | 1,678.0 | 1,667.0 | 3.1 | 8.0 |
| Cis-2-butane | 609.3 | 17.1 | 592.1 | 410.8 | 137.7 | 43.5 |
| High-boiling point materials** | 136.3 | 128.7 | — | — | — | — |
| Toluene | — | 1,900.3 | — | — | — | — |
| DMF | — | — | — | 0.6 | — | — |
| Sum | 57,347.1 | 31,340.8 | 27,895.4 | 10,090.3 | 190.8 | 17,192.1 |

TABLE 4

| | Amount of solvent used (ton/hr) | |
|---|---|---|
| Classification | Example 1 | Comparative Example 1 |
| Absorption separation part (toluene) | 18.4 | 237.6 |
| Purification part (DMF) | 290.0 | 160.0 |

TABLE 5

| | Total amount of energy used (Gcak/hr) | |
|---|---|---|
| Classification | Example 1 | Comparative Example 1 |
| Absorption separation part | 9.8 | 24.3 |
| Purification part | 44.7 | 35.4 |
| Sum | 54.4 | 59.8 |

TABLE 6

| | Example 1 | Comparative Example 1 |
|---|---|---|
| Energy unit per unit BD ($/ton) | 266 | 297 |

TABLE 7

| Classification | Example 1 | Comparative Example 1 |
|---|---|---|
| Recovery rate of butadiene | 94.1% by weight | 91.5% by weight |
| Purity of butadiene | 99.7% by weight | 99.7% by weight |

As shown in Table 4, in the case of Example 1 according to the present invention, butane is used as a diluent gas, and some hydrocarbons are recovered through compression and cooling in the condensation separation part. Accordingly, when hydrocarbons are recovered in the absorption separation part, the amount of the solvent used is significantly reduced in comparison with Comparative Example 1. On the other hand, in the case of the purification part, the amount of the solvent used in Example 1 is increased compared to that of Comparative Example 1 due to butane used as a diluent gas. However, as shown in Table 5, in the case of Example 1, the total amount of energy used in the absorption separation part and the purification part is greatly reduced as compared with Comparative Example 1.

In addition, as shown in Table 6, the energy unit per unit mass of butadiene in the butadiene preparation process is 266$/ton in Example 1 and 297$/ton in Comparative Example 1. That is, as compared with Comparative Example 1, energy consumption in Example 1 is significantly reduced.

In addition, as shown in Table 7, butadiene recovery rate in Example 1 is higher than that in Comparative Example 1, on the basis of when butadiene has the same purity. That is, in the case of Example 1, productivity and economic efficiency may be improved.

DESCRIPTION OF SYMBOLS

110, 210, 310, 410, 510, 610: OXIDATIVE DEHYDROGENATION REACTION PART
130, 250, 350, 450, 550, 650: ABSORPTION SEPARATION PART
120, 220, 320, 420, 520, 620: COOLING SEPARATION PART
230, 330, 430, 530, 630: CONDENSATION SEPARATION PART
140, 240, 340, 440, 540, 640: PURIFICATION PART
360, 460, 560, 660: DEGASIFICATION PART 370, 470, 570, 670: SOLVENT RECOVERY PART
480, 680: HIGH-BOILING POINT MATERIAL REMOVAL PART
531, 631: COMPRESSOR
532, 632: HEAT EXCHANGER

The invention claimed is:

1. A method of preparing butadiene, comprising:
passing a reaction raw materials stream containing butene, oxygen ($O_2$), steam, and butane as a diluent gas through an oxidative dehydrogenation reactor to oxidatively dehydrogenate the butene into oxidative dehydrogenation reaction products containing butadiene, water, n-butane, butene, COx and $O_2$;
removing water from the oxidative dehydrogenation reaction products by passing the oxidative dehydrogenation reaction products through a cooling separation part;
condensing hydrocarbons by passing the oxidative dehydrogenation reaction products, from which the water is removed, through a condensation separation part;
recovering all hydrocarbons not condensed in the condensation separation part by passing the oxidative dehydrogenation reaction products containing hydrocarbons not condensed in the condensation separation part through an absorption separation part; and
separating the butadiene by passing crude hydrocarbons comprising the n-butane, the butene, and the butadiene, which are condensed in the condensation separation part, and crude hydrocarbons comprising the n-butane, the butene, and the butadiene excluding the COx and the $O_2$, which are recovered in the absorption separation part, through a purification part,
wherein the n-butane and the butene excluding the butadiene, which are separated in the purification part, are fed again into the oxidative dehydrogenation reaction part.

2. The method according to claim 1, wherein the condensation separation part has a single-stage compression structure having one stage, and, in the condensation separation part, a compression discharge temperature is 50 to 250° C.

3. The method according to claim 1, wherein a refrigerant used in the condensation separation part is one or more selected from the group consisting of cooling water, ethylene glycol, an aqueous solution of ethylene glycol having a concentration of 20 to 100% by weight, propylene glycol, an aqueous solution of propylene glycol having a concentration of 30 to 100% by weight, and a propylene-based solvent.

4. The method according to claim 1, further comprising a step, in which a discharge stream containing crude hydrocarbons comprising n-butane, butene, and butadiene excluding COx and $O_2$, which are separated in the absorption separation part, is passed through the purification part to separate butadiene, and a gas containing residual n-butane is fed again into the oxidative dehydrogenation reaction part.

5. The method according to claim 1, wherein the step of separating COx and the $O_2$ by passing oxidative dehydrogenation reaction products containing hydrocarbons not condensed in the condensation separation part through the absorption separation part and the step of separating butadiene by passing hydrocarbons comprising n-butane, butene, and butadiene, which are condensed in the condensation separation part, through the purification part comprise:
a step, in which, in the absorption separation part, a discharge stream consisting of crude hydrocarbons comprising n-butane, butene, and butadiene excluding COx and $O_2$, which are present in a state absorbed in a solvent, is passed through a solvent recovery part to recover the solvent, and the recovered solvent is fed again into the absorption separation part;
a step, in which a discharge stream consisting of oxidative dehydrogenation reaction products containing a gas separated in the solvent recovery part and hydrocarbons condensed in the condensation separation part is passed through a degasification part to additionally separate COx and $O_2$;
a step of feeding COx and $O_2$ additionally separated in the degasification part into the absorption separation part; and
a step of feeding crude hydrocarbons comprising n-butane, butene, and butadiene excluding COx and $O_2$, which are additionally separated in the degasification part, into the purification part.

6. The method according to claim 5, wherein the degasification part or the solvent recovery part is operated by stripping using a general column or degasification.

7. The method according to claim 1, wherein the step of separating COx and $O_2$ by passing oxidative dehydrogenation reaction products containing hydrocarbons not condensed in the condensation separation part through the absorption separation part and the step of separating butadiene by passing hydrocarbons comprising n-butane, butene, and butadiene, which are condensed in the condensation separation part, through the purification part comprise:
a step, in which, in the absorption separation part, a discharge stream consisting of crude hydrocarbons comprising n-butane, butene, and butadiene excluding COx and $O_2$, which are present in a state absorbed in a solvent, is passed through a solvent recovery part to recover the solvent, and the recovered solvent is fed again into the absorption separation part;
a step, in which oxidative dehydrogenation reaction products containing a gas separated in the solvent recovery part and hydrocarbons condensed in the condensation separation part are passed through a degasification part to additionally separate COx and $O_2$;
a step of feeding COx and $O_2$ additionally separated in the degasification part into the absorption separation part;
a step of removing high-boiling point materials by passing crude hydrocarbons comprising n-butane, butene, and butadiene excluding COx and $O_2$, which are additionally separated in the degasification part, through a high-boiling point material removal part; and
a step of feeding crude hydrocarbons comprising n-butane, butene, and butadiene, in which the high-boiling point materials are removed, into the purification part.

8. The method according to claim 1, wherein the step of separating COx and $O_2$ by passing oxidative dehydrogenation reaction products containing hydrocarbons not condensed in the condensation separation part through the absorption separation part and the step of separating butadiene by passing hydrocarbons comprising n-butane, butene, and butadiene, which are condensed in the condensation separation part, through the purification part comprise:
a step, in which, in the absorption separation part, a discharge stream consisting of crude hydrocarbons comprising n-butane, butene, and butadiene excluding COx and $O_2$, which are present in a state absorbed in a solvent, is passed through a solvent recovery part to recover the solvent, and the recovered solvent is fed again into the absorption separation part;
a step, in which oxidative dehydrogenation reaction products containing a gas separated in the solvent recovery part and hydrocarbons condensed in the condensation separation part are passed through a degasification part to additionally separate COx and $O_2$;

a step of feeding COx and $O_2$ additionally separated in the degasification part into a condensation system; and a step of feeding crude hydrocarbons comprising n-butane, butene, and butadiene excluding COx and $O_2$, which are additionally separated in the degasification part, into the purification part.

9. The method according to claim 1, wherein the step of separating COx and $O_2$ by passing oxidative dehydrogenation reaction products containing hydrocarbons not condensed in the condensation separation part through the absorption separation part and the step of separating butadiene by passing hydrocarbons comprising n-butane, butene, and butadiene, which are condensed in the condensation separation part, through the purification part comprise:

a step, in which, in the absorption separation part, a discharge stream consisting of crude hydrocarbons comprising n-butane, butene, and butadiene excluding COx and $O_2$, which are present in a state absorbed in a solvent, is passed through a solvent recovery part to recover the solvent, and the recovered solvent is fed again into the absorption separation part;

a step, in which COx and $O_2$ separated in the solvent recovery part and hydrocarbons condensed in the condensation separation part are passed through a degasification part to additionally separate COx and $O_2$;

a step of feeding COx and $O_2$ additionally separated in the degasification part into a condensation system;

a step of removing high-boiling point materials by passing crude hydrocarbons comprising n-butane, butene, and butadiene excluding COx and $O_2$, which are additionally separated in the degasification part, through a high-boiling point material removal part; and a step of feeding crude hydrocarbons comprising n-butane, butene, and butadiene, in which the high-boiling point materials are removed, into the purification part.

10. The method according to claim 1, further comprising a step, in which butene remaining after butadiene is separated in the purification part and butene supplied as a raw material are combined and fed into the oxidative dehydrogenation reaction part.

11. The method according to claim 1, wherein the oxidative dehydrogenation reaction part is operated at a reaction temperature of 150 to 650° C. under isothermal or adiabatic conditions, in which case butene, oxygen ($O_2$), steam, and n-butane are used as reaction raw materials and a ferrite catalyst is used as a catalyst, wherein n-butane is a residue remaining after butadiene is separated in the purification part and is fed again into the oxidative dehydrogenation reaction part.

12. The method according to claim 1, wherein the cooling separation part is operated by a quenching-type direct cooling system (quencher) or an indirect cooling system.

13. The method according to claim 1, wherein the absorption separation part is operated in an absorption manner, in which a solvent for separating COx and $O_2$ is used.

14. The method according to claim 1, wherein the condensation separation part has a multistage compression structure having 1 to 10 stages, and, in the condensation separation part, a compression discharge temperature is 50 to 250° C.

15. The method according to claim 1, wherein the condensation separation part has a multistage compression structure having 2 stages, and, in the condensation separation part, a compression discharge temperature is 50 to 250° C.

16. A method of preparing butadiene, comprising:

passing a reaction raw materials stream containing butene, oxygen ($O_2$), steam, and butane as a diluent gas through an oxidative dehydrogenation reactor to oxidatively dehydrogenate the butene into oxidative dehydrogenation reaction products containing butadiene, water, n-butane, butene, COx and $O_2$;

removing water from the oxidative dehydrogenation reaction products by passing the oxidative dehydrogenation reaction products through a cooling separation part;

condensing hydrocarbons by passing the oxidative dehydrogenation reaction products, from which the water is removed, through a condensation separation part;

recovering all hydrocarbons not condensed in the condensation separation part by passing the oxidative dehydrogenation reaction products containing hydrocarbons not condensed in the condensation separation part through an absorption separation part; and separating the butadiene by passing crude hydrocarbons comprising the n-butane, the butene, and the butadiene, which are condensed in the condensation separation part, and crude hydrocarbons comprising the n-butane, the butene, and the butadiene excluding the COx and the $O_2$, which are recovered in the absorption separation part, through a purification part, wherein the n-butane and the butene excluding the butadiene, which are separated in the purification part, are fed again into the oxidative dehydrogenation reaction part, wherein, in the oxidative dehydrogenation reaction part, the oxidative dehydrogenation is performed in a molar ratio of butene:oxygen:steam:diluent gas=1:0.5 to 3:0.1 to 20:0.1 to 20.

* * * * *